(12) United States Patent
Sheardown et al.

(10) Patent No.: US 8,920,841 B2
(45) Date of Patent: Dec. 30, 2014

(54) BIODEGRADABLE POLYMER SYSTEM

(76) Inventors: Heather Sheardown, Nobleton (CA); Scott Fitzpatrick, Oshawa (CA); M.A. Jafar Mazumder, Pointe-Claire (CA)

(*) Notice: Subject to any disclaimer, the term of this patent is extended or adjusted under 35 U.S.C. 154(b) by 146 days.

(21) Appl. No.: 13/064,873

(22) Filed: Apr. 22, 2011

(65) Prior Publication Data
US 2011/0288062 A1 Nov. 24, 2011

Related U.S. Application Data

(60) Provisional application No. 61/327,326, filed on Apr. 23, 2010.

(51) Int. Cl.
| A61K 9/14 | (2006.01) |
| A61K 31/56 | (2006.01) |
| A61K 31/74 | (2006.01) |
| A61K 9/00 | (2006.01) |
| A61K 47/48 | (2006.01) |
| A61K 47/32 | (2006.01) |
| A61K 31/573 | (2006.01) |

(52) U.S. Cl.
CPC .............. *A61K 31/573* (2013.01); *A61K 9/0051* (2013.01); *A61K 47/48176* (2013.01); *A61K 47/32* (2013.01)

USPC ..... 424/486; 514/180; 424/78.18; 424/78.31; 424/78.04; 424/78.02

(58) Field of Classification Search
CPC ..... A61K 9/0012; A61K 9/0024; A61K 9/08; A61K 9/10; A61K 9/107; A61K 9/0051; A61K 47/48176; A61K 47/32; A61K 31/573; A61K 51/121
USPC ............. 424/486, 78.18, 78.31, 78.04, 78.02; 514/180
See application file for complete search history.

(56) References Cited

U.S. PATENT DOCUMENTS

2008/0255305 A1* 10/2008 Brook et al. .................. 525/103

OTHER PUBLICATIONS

Machine Translation for CN 101422433, May 2009 (Google).*
Machine Translation for CN 101422433, May 2009 (espacenet).*
Cui et al. ("New Hydrolysis-Dependent Thermosensitive Polymer for an Injectable Degradable System" in Biomacromolecules 2007, 8, 1280-1286).*

* cited by examiner

*Primary Examiner* — Blessing M Fubara

(57) ABSTRACT

A polymer system useful for in vivo delivery of a therapeutic agent is provided. The polymer system comprises a biocompatible biodegradable polymeric backbone that is capable of a reversible stimuli-induced transition from liquid to gel.

13 Claims, 8 Drawing Sheets

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: cell adhesion agent

<400> SEQUENCE: 1

Arg Gly Asp Ser
1

<210> SEQ ID NO 2
<211> LENGTH: 4
<212> TYPE: PRT
<213> ORGANISM: Artificial Sequence
<220> FEATURE:
<223> OTHER INFORMATION: cell adhesion agent

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: cell adhesion agent

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: cell adhesion agent

<400> SEQUENCE: 4

Ile Lys Val Ala Val
1               5

<210> SEQ ID NO 5
<211> LENGTH: 5
<212> TYPE: PRT
<213> ORGANISM: Artificial Sequence
<220> FEATURE:
<223> OTHER INFORMATION: cell adhesion agent

<400> SEQUENCE: 5

Gly Phe Gln Gly Arg
1               5
```

US 8,920,841 B2

BIODEGRADABLE POLYMER SYSTEM

FIELD OF THE INVENTION

The present invention relates to polymer systems, and in particular, to biodegradable polymer systems that are useful for drug and cell delivery.

BACKGROUND OF THE INVENTION

Efficient delivery of pharmaceuticals to the back of the eye is one of the most significant unmet needs of visual health care. Recently, there have been significant advances in the field of ophthalmic pharmaceuticals, with the development of vascular endothelial growth factor (VEGF) antagonists capable of minimizing ocular neovascularization, corticosteroids that can combat macular edema, and others such as antioxidants and hypertensive drugs. However, conventional drug delivery modalities are extremely inefficient for delivering therapeutically relevant doses of these advanced pharmaceuticals to affected tissues in the back of the eye.

Delivery of drugs to the posterior chamber of the eye is made difficult by the isolated nature of the eye, which is separated from systemic circulation by blood ocular barriers, the blood retinal barrier (BRB) and blood aqueous barrier (BAB). Furthermore, the eye is a segmented structure with numerous barriers to delivery and effective clearance mechanisms that effectively eliminate pharmaceuticals that successfully reach the posterior chamber. The segmented eye is divided into anterior and posterior regions. The anterior chamber is composed of the cornea, ciliary body, aqueous humor and the lens, whereas the posterior segment contains the choroid, vitreous body, and the retina. Topically applied drugs enter the anterior chamber by crossing the cornea, or through the conjunctiva and sclera. Drugs can also enter the anterior chamber from the systemic circulation, but must cross the BAB. Drugs are cleared from the anterior chamber via aqueous turnover, or by re-absorption into systemic circulation. The half-life of a typical drug within the aqueous of the anterior chamber is roughly one hour. Drugs can be introduced into the posterior segment through systemic circulation by crossing the BRB, through non-corneal permeation into the uvea or by direct injection into the vitreous. Drug clearance from the posterior segment occurs through either the anterior or posterior route. The anterior route involves diffusion across the vitreous and elimination via uveal blood flow and aqueous turnover, whereas elimination via the posterior route requires permeation through the BRB.

As a result of these numerous barriers, effective clearance routes and the segmented nature of the eye, delivery of drugs to the posterior segment is particularly challenging. Topically applied eye drops typically result in less than 5% uptake into the anterior chamber and negligible amounts enter the back of the eye. Systemically applied drugs are also severely limited in their ability to reach the back of the eye; only 1-2% of a systemically applied dose crosses the restrictive blood ocular barriers. Therefore, excessive systemic doses are required to achieve therapeutic concentrations of drug within the posterior segment of the eye. Furthermore, many new pharmaceuticals are protein-based and are therefore not suitable for oral delivery as they are rapidly denatured in the digestive system.

Direct injection into the vitreous cavity is a highly efficient technique to introduce therapeutically relevant doses of drug into the vitreous body and retinal tissues. However, due to the effective clearance mechanisms, frequent injections (every 4-6 weeks) are often required to maintain therapeutically relevant concentrations. While intravitreal injections are an acceptable means of delivery, frequent injections are associated with increased risk of complications such as endophthalmitis, cataract formation, vitreous hemorrhage, retinal detachment and patient discomfort.

In view of the foregoing, there is a need for drug delivery approaches that safely utilize the intravitreal route to provide localized delivery of therapeutics for sustained periods of time that do not require frequent perforation of the eye wall to deliver pharmaceuticals to the back of the eye to treat numerous debilitating ocular conditions.

SUMMARY OF THE INVENTION

A biodegradable polymer system has now been developed that is useful for the in vivo delivery of therapeutic agents.

Accordingly, in one aspect of the invention a polymer system useful for in vivo delivery of a therapeutic agent is provided wherein the polymer system comprises a polymeric backbone, and wherein the polymer system is capable of reversible stimuli-induced phase transition from liquid to gel.

In another aspect of the invention, a method of delivering a therapeutic, agent to a target site in vivo is provided comprising administering an aqueous biocompatible polymer solution to the target site, wherein the polymer incorporates a therapeutic agent and a component that is degradable over time, and wherein the polymer system is capable of reversible stimuli-induced phase transition from liquid to gel.

These and other aspects of the invention are described by reference to the following figures.

DETAILED DESCRIPTION OF THE INVENTION

Figure 1:
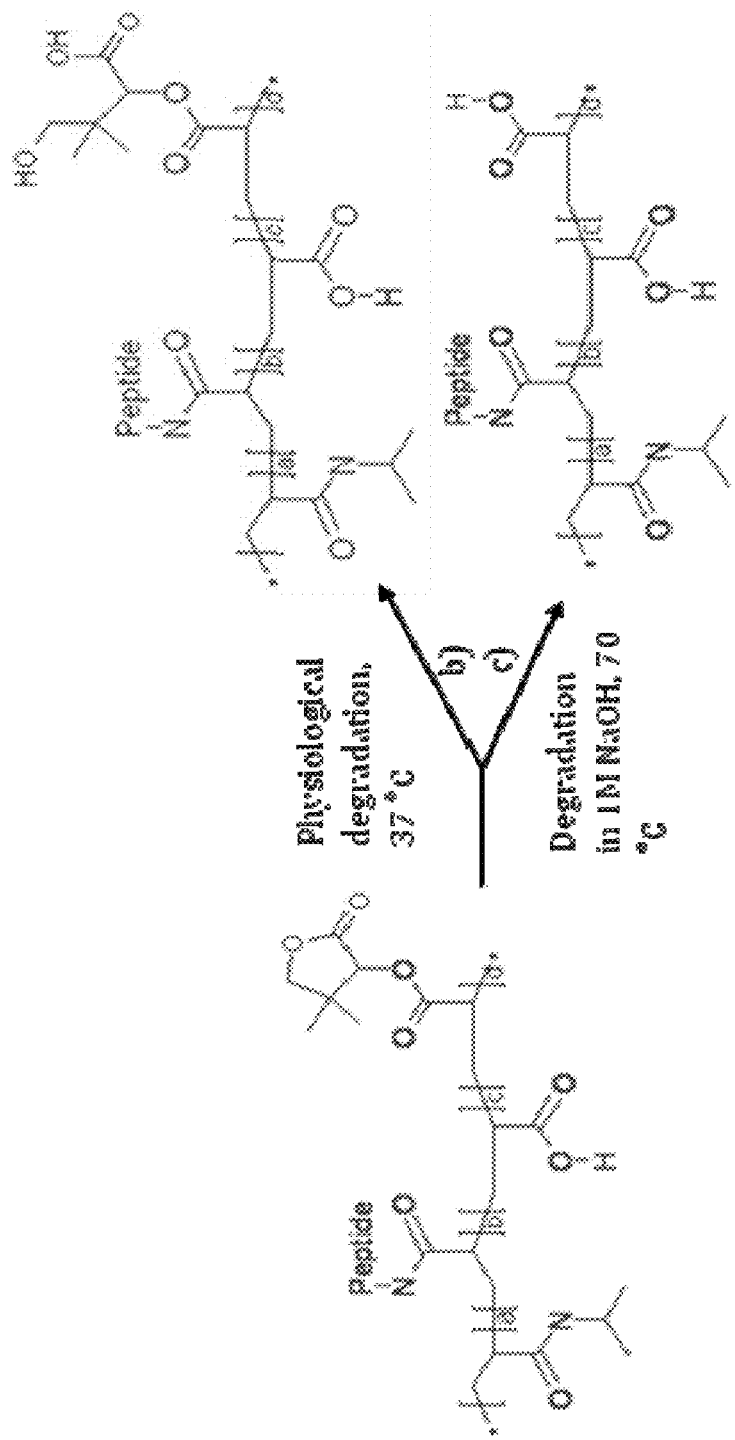
FIG. 1 illustrates a proposed degradation mechanism of pNNAD copolymers in physiological conditions b) and under harsh basic conditions employed in an accelerated degradation experiment c)

A polymer system useful for in vivo delivery of a therapeutic agent is provided. The polymer system comprises a biocompatible polymeric backbone that is capable of reversible stimuli-induced phase transition from liquid to gel.

The biocompatible polymeric backbone comprises monomers that form polymers to yield a polymer that is capable of a reversible transition from a liquid to a gel on exposure to a stimuli such as heat or light. The term "reversible" is used herein to indicate that following a transition from liquid to gel (e.g. gelation), the polymer system is capable of resorption, or transition back to a liquid from the gel phase. Suitable such transition monomers include, but not limited to, acrylic-based polymers such as polymethylmethacrylate, poly(hydroxyethyl methacrylate) (pHEMA), poly N-isopropyl acrylamide (NIPAAm), polyacrylic acid; polyurethanes and polyurethane ureas; silicone polymers and acrylic-based polymers such as pHEMA comprising various amounts of TRIS varying from about 1% to 99% TRIS; other hydrogel polymers including polyvinyl alcohol and protein-based biopolymers such as collagen.

The polymeric backbone may also comprise a co-monomer component that is degradable over time. Examples of degradable co-monomers include, but are not limited to, acryloyloxy dimethyl-γ-butyrolactone (DBA) and other lactone-containing materials as well as materials such as poly(lactic acid), poly(glycolic acid), poly(glycolic-co-lactic acid), poly(caprolactone), [poly(dioxanone), poly(3-hydroxybutyrate), poly(3-hydroxyvalcrate), poly(valcrolactone), poly(tartonic acid), poly(malonic acid)], poly(anhydrides), poly(orthoesters) and polyphosphazenes.

Additional hydrophilic co-monomer (e.g. acrylic acid and the like) may also be incorporated into the polymer backbone to balance a hydrophobic degradable co-monomer (e.g. DBA and other lactone-containing monomers). As the hydrophobic content of the copolymer increases, the critical temperature (LCST) at which the polymer solution transitions from a liquid to a gel decreases. Thus, balancing the hydrophilic and hydrophobic content of the polymer may be desirable to attain an appropriate transition temperature of the polymer. For example, for use of the polymer system in vivo, a transition temperature of about body temperature or slightly below is appropriate. Accordingly, the hydrophilicity of the polymer system may require adjustment in order to attain a transition temperature within this range.

The polymeric backbone may additionally comprise a co-monomer component that provides binding sites suitable for conjugation of a therapeutic agent thereto. The term "therapeutic agent" is used herein to denote drugs such as drugs useful to treat ophthalmic conditions, proteins such as growth factors and antibodies, as well as biologic molecules such as cells. In one embodiment, the therapeutic-binding co-monomer is an amine-reactive co-monomer such as a succinide-containing monomer, e.g. N-acrylic acid N-hydroxysuccinimide (NAS).

The backbone polymer may be synthesized using free radical polymerization, a technique known to those of skill in the art. Generally, the selected co-monomers are combined to form a co-monomer solution which is then heated with mixing for a sufficient period of time to form a polymer solution. The amounts of each of the co-monomer components of the backbone are such as to result in a polymer that is degradable over time, which is capable of reversible stimuli-induced phase transition from liquid to gel, and which may optionally have binding sites suitable for conjugation to a therapeutic agent. Exemplary amounts of each co-monomer component within the polymer backbone are as follows: about 50-99.5% by weight of a co-monomer(s) which is capable of stimuli-induced transition from liquid to gel, preferably at least about 60-70%, and more preferably at least about 75-95% by weight of such transitional monomer(s), about 0.5-15% by weight of a degradable co-monomer component, optionally an amount of about 0-15% by weight of a component that provides binding sites suitable for conjugation of a therapeutic agent, and preferably, about 0.5-5% by weight of such a co-monomer, and optionally an amount of about 0-15% of a hydrophilic co-monomer.

The polymer solution is suitable for administration to an in vivo target site and phase transition from liquid to gel is induced when the solution is exposed to a gel-inducing stimulus. In this regard, gelation may be temperature-induced, and the characteristics of the polymer are such that at above a certain temperature, gelation occurs. The gelation-inducing temperature may be in the range of about around 10-37° C. In one embodiment, the application of heat to an acrylamide (e.g. N-isopropylacrylamide/acrylic acid) polymer solution, results in gelation of the solution. For in vivo use, the solution preferably gels at a temperature that is greater than room temperature, such as a temperature between room temperature and body temperature, around 27-32 degrees Celsius, or a temperature that is slightly less than physiological temperature up to physiological temperature, e.g. in the range of about 33-37.5° C., to render it suitable and convenient for use in vivo, e.g. gelling on administration to an in vivo target site.

Alternatively, the polymer solution may be admixed with an initiating agent that is sensitive to a given stimulus, such as heat or light, to result in gelation of the solution. In one embodiment, a photo-initiator may be added to the polymer solution to impart photo-sensitivity to the polymer solution. Examples of suitable photo-initiators include, but are not limited to, 2,2-dimethoxy-2-phenylacetophenone (DMPA), benzophenone and IRGACURE™. Generally the amount of photo-initiator added to the polymer solution is an amount sufficient to cause gelation thereof on exposure to UV radiation, for example, an amount in the range of about 0.5-2% by weight of the polymer solution. For in situ polymerization, the photo-sensitive polymer solution is injected into a target site and exposed to UV light. The wavelength of UV light used for gelation will depend on the photo-initiator used. For the photo-initiator; DMPA, a wavelength of about 365 nm is used.

The present system may be conjugated to an agent which facilitates cell adhesion. Such agents include, but are not limited to, amine-terminated agents, cell-adhesion peptides such as RGDS, REDV, YIGSR, IKVAV and GFOGER. Facile conjugation of the cell adhesion agent is achieved via coupling to a recipient site on the polymer. For example, conjugation of cell adhesion peptides may be achieved through coupling with an amine-reactive co-monomer such a succinimide-containing monomer, e.g. N-acrylic acid N-hydroxysuccinimide.

A method of delivering a therapeutic agent to a target site in vivo is provided using a biocompatible polymer system as described. The method comprises administering a biocompatible polymer solution to the target site, wherein the polymer is degradable over time, is capable of reversible stimuli-induced phase transition from liquid to gel, and incorporates a therapeutic agent. The method is particularly useful for ophthalmic delivery of therapeutic agents, e.g. to treat posterior segment conditions. In this regard, the in situ gelling polymer solution, in combination with a therapeutic agent, is delivered into the eye in a minimally invasive fashion. In situ gelation, caused by physiological temperatures, will entrap the therapeutic agent (e.g. cell and drug suspension), for delayed release over a period of time. This will be followed by degradation of the polymer backbone which will promote clearance of the polymer from the eye and body.

The volume of polymer solution administered to a target site will be selected based on the intended application. Thus, for use in the delivery of cells or a therapeutic agent, a volume of the polymer solution suitable to deliver the required dose of cells or therapeutic agent will be administered, as well as an amount suitable to retain the cells and/or agent at the target site, as required.

Thus, the present polymeric system provides a system which under physiological conditions degrades slowly and does not break down into small molecular weight byproducts as the polymer degrades. 'Degradation' is achieved through a simple transition in copolymer phase transition properties induced by a change in reaction within the polymer, for example, via ring opening of the lactone-containing component in the copolymer, such as DBA, followed by re-hydration of the gelled scaffold. It is noted that, under harsh basic conditions, an accelerated degradation process may be apt to occur; however, this may be avoided if reactive functional groups in the polymer are capped to prevent reaction, for example, using peptide conjugation as set out, amine functionalized short chain PEG or similar conjugation.

Embodiments of the present invention are described in the following specific example which is not to be construed as limiting.

Example 1

Materials and Methods

N-acrylic acid N-hydroxysuccinimide (NAS), (R)-α-acryloyloxy-β-β-dimethyl-γ-butyrolactone (95%) (DBA), benzoyl peroxide (BPO, 97%), dexamethasone (98%) and Bovine Serum Albumin (66 kDa) were purchased from Sigma-Aldrich (Oakville, ON, Canada), and used as received. N-isopropylacrylamide (NIPAAm) (97%) was purchased from Sigma-Aldrich (Oakville, ON, Canada), and was purified by recrystallization from a toluene/hexane mixture. Acrylic Acid (AA) (99%) was purchased from Sigma-Aldrich (Oakville, ON, Canada), and was purified by passing the monomer through a packed column containing Sigma-Aldrich inhibitor remover to remove the 4-methoxyphenol (MEHQ) polymerization inhibitor. The cell adhesion peptide, RGDS (433.4 Da) was purchased from American Peptide (Sunnyvale, Calif., USA), and was used as received. 1,4-dioxane, toluene, hexane, tetrahydrofuran (THF), dimethylsulfoxide (DMSO) and anhydrous ethyl ether were purchased from Calcdon Laboratories (Calcdon, ON) and were used as received. Sodium hydroxide and hydrochloric acid solutions were purchased as concentrates from Anachemia Chemical (Rouses Point, N.Y., USA), and were prepared by diluting to 1.0 or 0.1M with deionized water. Deionized water with a resistivity of 18.2 MΩ cm was prepared using a Milli-pore. Barnstead water purification system (Graham, N.C., USA). All glassware was cleaned using deionized water. Phosphate buffered saline solution (PBS, pH 7.4) was obtained from McMaster University Health Science facilities and used as received. Cellulose dialysis membranes with molecular weight cutoff values ranging from 1 to 12 kg/mol were purchased from Spectrum Laboratories Inc (Rancho Dominguez, Calif., USA).

Synthesis of p(NIPAAm-NAS-AA-DBA) Copolymers

Poly(NIPAAm-NAS-AA-DBA) (pNNAD) copolymers were synthesized via free radical polymerization in a 100 ml one-necked round bottom flask. NIPAAm (3.84 g, 33.95 mmol), NAS (0.287 g, 1.69 mmol), AA (0.244 g, 3.39 mmol), DBA (0.626 g, 3.39 mmol) and BPO (0.103 g, 0.42 mmol, 1 mol % relative to monomer content) were dissolved in 45 mL 1,4-dioxane to form a 10 wt % monomer solution (90:4:8:8 molar feed ratio of NIPAAm:NAS:AA:DBA). Dry nitrogen was bubbled through the solution for 15 minutes, the flask was sealed and subsequently heated to 70° C. for 24 hours in a temperature controlled oil bath with constant stirring to provide uniform mixing. Following the reaction, the polymer solution was cooled to room temperature and isolated by precipitation in anhydrous ethyl ether (1 L). The resulting polymer, denoted pNNAD-8, wherein the number represents the copolymer DBA content, was dried overnight in a vacuum oven at 50° C. The copolymer was further purified by repeated precipitation from THF into anhydrous ethyl ether. The purified copolymer was then dried to a constant weight in a vacuum oven at 50° C. pNNAD-8 yield was 4.5 g (90%).

Copolymerization and purification of pNNAD copolymers with NIPAAm:NAS:AA:DBA molar feed ratios of 80:4:12:4 (pNNAD-4) and 80:4:4:12 (pNNAD-12) were prepared in a similar fashion to pNNAD-8. Copolymer yield of pNNAD-4 and pNNAD-12 was 93% (4.65 g) and 87% (4.35 g) respectively.

For in vitro and in vivo testing purposes, pNNAD copolymers were further purified by extensive dialysis in deionized water at 4° C. using cellulose tubing possessing a 3.5 kg/mol MW cut-off. The resulting copolymer solutions were freeze-dried, and stored frozen at −20° C. until use.

Preparation of RGDS Grafted pNNAD Copolymers

Cell-adhesive RGDS peptides were grafted onto the pNNAD copolymers via conjugation reaction between amine groups present on the arginine residues and copolymer NAS groups. Briefly, pNNAD-12 (0.9017 g, 0.289 mmol NAS) was dissolved in 40 mL PBS (pH 7.4) in a 100 mL one neck round bottom flask. RGDS (80 mg, 0.184 mmol) was dissolved in 5 mL PBS (pH 7.4), and added to the polymer solution under stirring. The reaction mixture was allowed to proceed for 24 hours at 4° C. under continuous stirring. The RGDS grafted copolymer, pNNAD-12-RGDS, was extensively dialyzed against deionized water at 4° C. using cellulose membranes with a 3.5 kg/mol MW cut-off. The resulting polymer solution was freeze-dried, and stored at −20° C. The RGDS grafting density on the pNNAD-12 copolymer was determined to be 1.7 mol % of the total monomer content by $^1$H NMR.

RGDS was grafted onto the pNNAD-4 copolymer in a similar fashion. pNNAD-4 (0.899 g, 0.313 mmol NAS), and RGDS (81 mg, 0.186 mmol) were dissolved in 45 ml PBS (pH 7.4) and stirred continuously at 4° C. for 24 hours. The resulting pNNAD-4-RGDS copolymer was then dialyzed extensively against deionized water at 4° C. using cellulose membranes with a 3.5 kg/mol MW cut-off and then freeze-dried and stored at −20° C. The RGDS grafting density on the pNNAD-4 copolymer was determined to be 2 mol % of the total monomer content by $^1$H NMR.

Material Characterization

The pNNAD copolymer structures were characterized using a Thermo Fisher Nicolet 6700 Fourier Transform Infrared (FT-IR) spectrometer. Copolymer compositions and the extent of RGDS grafting were determined by $^1$H NMR using a Bruker AV 600 spectrometer with DMSO-d6 as a solvent. Copolymer molecular weights were determined by gel permeation chromatography (GPC) using a Waters system consisting of a 515 HPLC pump, 717 plus Autosampler, three Ultrahydrogel columns (0-3, 0-50, 2-300 kDa), and a 2414 refractive index detector. Copolymers were first hydrolyzed via accelerated degradation (described in the Degradation by Accelerated Hydrolysis section) to remove phase transition properties. Samples were then eluted with 20 mM PBS buffer, 100 mM NaNO$_3$ at pH 7.2 using a flow rate of 0.8 mL/min, and the system was calibrated with commercially available narrow dispersed molecular weight polyethylene glycol (PEG) standards (Waters, Mississauga, ON).

Lower Critical Solution Temperature Characterization

Characterization of copolymer LCST was carried out using differential scanning calorimetry (DSC, TA Instruments 2910) and UV/vis spectrophotometry (Cary 300). For DSC, samples were dissolved in PBS to 20% and were heated from 0 to 70° C. at a rate of 2° C./min in hermetic pans. The thermal transition temperature was considered to be the temperature at which the maximum endothermal peak in the DSC curve was observed. For UV spectrophotometry, the copolymer cloud point was utilized to assess changes in transmittance as a function of temperature. Copolymers were dissolved in PBS (10% w/v) and kept at 4° C. for 24 hours. The copolymer solutions were then placed in 4 mL UV cuvettes and degassed briefly via sonication. The samples were then heated from 10 to 45° C. with a heating rate of 1° C./min. Transmittance measurements were recorded every thirty seconds.

Glass transition temperatures (Tgs) of intact and degraded copolymers (~8 mg) were measured by DSC (TA Instruments 2910) over a temperature range of −10 to 200° C. with a heating rate of 10° C./min.

Water Content

The water content of the PNNAD copolymers was assessed gravimetrically. Samples were dissolved in de-ionized water (15% w/v) and placed in pre-weighed polystyrene dishes. The covered dishes were then placed in a 37° C. oven to induce hydrogel gelation. After 6 hours, supernatant surrounding the gelled hydrogels was aspirated and the pellets were carefully blotted dry with tissue paper to remove any surface water. The samples were placed back in their respective dishes and weighed to obtain the wet mass. The samples were then dried to constant weight in a 65° C. oven. Hydrogel water content was assessed using the following equation:

$$\text{Water Content} = \frac{(m_w - m_d)}{m_d} * 100\% \quad \text{(Equation 1)}$$

where $m_w$ is the hydrogel's wet mass and $m_d$ is the dry mass.

Degradation by Accelerated Hydrolysis:

Accelerated hydrolysis, both complete and partial, of the pNNAD copolymers was performed following ISO 10993. Briefly, solutions of each polymer were prepared in de-ionized water (20% w/v) in a 20 ml glass vial. The pH was adjusted to 10.5 (with either 0.1 or 1 M NaOH) and then placed in an oven at 70° C. The pH of the polymer solution was adjusted to 10.5 daily. Complete degradation of the copolymers was achieved in 21 days at which point, the pH of the solution remained constant. Fully degraded samples were maintained at pH 10.5 for another three days (24 in total) and collected by dialysis with 3.5 kg/mol MW cut-off and freeze-drying. During the degradation process, aliquots were collected periodically, dialyzed and freeze-dried to determine the composition of the partially degraded polymers. Partially degraded pNNAD samples presented in this text were collected from copolymers subjected to 10 days of accelerated degradation.

Copolymer Degradation in Heated PBS

Copolymers were dissolved in PBS to concentrations of 20% (100 mg in 0.5 ml) in pre-weighed 2 mL plastic epindorf tubes. The samples were dissolved in a 4° C. fridge for 24 hours and then placed in a 37° C. oven and allowed to gel. After 5, 20, 40, 65 and 130 days of incubation at 37° C., the supernatant was aspirated and samples were carefully rinsed with pre-warmed milli-Q water to remove any soluble pNNAD and PBS residue. The rinsed samples were then carefully blotted dry with a tissue paper to remove any residual surface water and the resulting polymer wet mass $m_{wf}$ was obtained. The samples were then dried to a constant weight in a 65° C. oven, to obtain the final polymer dry mass, $m_{df}$. Polymer degradation was determined using the following equation:

$$\text{Mass Remaining} = \frac{m_{df}}{m_{di}} \times 100\% \quad \text{(Equation 2)}$$

where $m_{di}$ denotes the mass of the initial dry sample. Water content of the final copolymer was quantified according to equation 1.

Copolymer Morphology

A Phillips 515 scanning electron microscope (SEM) was used to visualize physical changes in polymer morphology as a function of degradation. Dried polymer samples from the PBS degradation experiment were collected for analysis and a 10 nm platinum coating was applied to the surface of the degraded copolymer samples to allow surface visualization. Images were captured using Mektech URSA 100 Rev. 1.30 imaging software.

Dexamethasone Release Assay

Dexamethasone was dissolved in PBS to form a 10% w/v solution. The pNNAD copolymers were then dissolved to concentrations of 20% w/v (100 mg in 0.5 mL) in the PBS/dexamethasone solution. The samples were placed in a 4° C. fridge until the copolymers had fully dissolved. The drug-infused copolymer solutions were then placed in a 37° C. oven for two hours to drive scaffold formation and drug entrapment. The supernatant was then collected and the copolymers were rinsed once with a pre-warmed PBS solution. The PBS wash was then removed and replaced with 1 mL of fresh, pre-warmed PBS to start the release curve. Aliquots (100 μl) were removed at 0.5, 1, 2, 3, 4, 5, 6 hours into the release and were then taken less frequently throughout the duration of the experiment. Fresh, pre-warmed 100 μl aliquots were added to the vials to restore the volume of the sample. Samples were analyzed using a Waters high performance liquid chromatography (HPLC) system with a 2707 autosampler, 2489 UV spectrophotometer, Atlantis dC18 5 μm, 4.6×100 mm column and Breeze 2 software. The mobile phase, a 40% v/v HPLC-grade acetonitrile in water solution, was passed through a 0.45 μm filter and de-gassed via sonication prior to use. A 1.0 ml/ml isocratic flow-rate was employed with 100 μl sample injection volumes and a 254 nm detection wavelength. Sample concentrations were assessed relative to a standard calibration curve of dexamethasone prepared in mobile phase.

Cell Culture

Human retinal pigment epithelial (RPE) cells (CRL-2502, ATCC, Manasass, Va.) were cultured in a temperature-controlled $CO_2$ incubator (37° C., 5% $CO_2$, 95% air, 100% humidity). Cell culture medium (DMEM-F12) was collected from McMaster University Health Science facilities and was supplemented with fetal bovine serum (FBS) (6.25% final concentration, Gibco), 1× glutamate (1% final concentration, Gibco) penicillin-streptomycin (1% final concentration, Gibco), and sodium biocarbonate (0.8% final concentration, Gibco). Prior to testing, samples were extensively dialyzed in deionized water with cellulose tubing (3.5 kg/mol MW cut-off, Spectrum Laboratories), freeze-dried and then pre-treated with a solution of PBS and penicillin-streptomycin (3:1 v/v). RPE cells were seeded with fresh, supplemented DMEM-F12 culture medium in a 48 well tissue culture polystyrene (TCPS) dish at a density of 50,000 cells per well.

After a 2 hour incubation period, which allowed cells to adhere to the bottom of the TCPS dish, the cell supernatant was removed and replaced with fresh media containing 10 mg of dissolved copolymer. Test conditions included partially degraded, fully hydrolyzed and intact pNNAD-4, pNNAD-8 and pNNAD-12 copolymers. Fresh culture medium containing no polymer was used as a control. Samples were then returned to the incubator. Viability was assessed after 96 hours using a Trypan Blue exclusion assay (0.4%, Gibco). A one-factor analysis of variance (ANOVA) was used to analyze scaffold impact on RPE viability using an ☐=0.05. Statistical analysis was performed using PASW Stastics 18 (SPSS, Inc., Il). Error bars on all graphs represent standard deviation.

Subcutaneous Injections in SKH1-E Mice

Following extensive dialysis and freeze-drying, samples were sterilized with ethylene oxide (EO) gas for subsequent in vivo testing. EO sterilization was achieved at the McMaster University histopathology laboratory. Samples were exposed to a 100% EO atmosphere at 57° C. for 2 hours followed by exposure to sterile air for 15 hours to evaporate residual EO. Copolymers pNNAD-4, pNNAD-12, pNNAD-4-RGDS and pNNAD-12-RGDS were dissolved in Fischer Brand medical grade saline to concentrations of 15% w/v in 10 mL aliquots. Polymer samples, syringes and the injection site were pre-cooled with ice to prevent premature polymer gelation during injection. Hairless SKH1-E (strain code 447) mice were anaesthetized with isoflurane gas and 150 ☐l polymer suspensions were injected subcutaneously between the shoulder blades. The mice were sacrificed at day 20 and 40, and the tissue at the injection site was excised, fixed in a 4% formalin solution for 24 hours and then embedded within paraffin wax. These tissues were then sliced into 4 ☐m sections using a Leica RM2255 microtome and stained with hematoxylin and eosin (H&E). Images of the stained and processed tissue from the injection site were captured using an Olympus BX51 optical microscope with a Q Imaging Retiga 2000R and Image-Pro Plus (version 7.0) imaging software.

Results and Discussion

The proposed mechanism of ophthalmic drug release from thermoresponsive pNNAD copolymers is illustrated in the following example. A PNIPAAm solution infused with Toluidine Blue was injected into a pre-heated aqueous solution. Gel formation occurred rapidly following injection into the aqueous environment, entrapping the infused toluidine dye, which acts as a representative drug for visualization purposes. The toluidine solution was then slowly released from the pNNAD copolymer into the surrounding environment. Upon depletion of the majority of the toluidine reservoir, hydrolytic opening of the DBA lactone ring induced copolymer re-hydration, which would then lead to clearance from the eye and body.

Polymer Structure and Characterizations:

Copolymers with varying compositions of NIPAAm, NAS, AA and DBA were synthesized via free radical polymerization in 1,4-dioxane using BPO as an initiator. The final composition of the various pNNAD copolymers was determined using $^1$H NMR and the values, which were found to be similar to the co-monomer feed ratios, are reported in Table 1.

TABLE 1

Polymer feed ratios, final copolymer composition, molecular weight determined by GPC and phase transition temperatures determined with DSC.

| Polymer (feed ratio) NIPAAM-NAS-AA-DBA | Composition[a] | MW ($M_n$) (kg/mol)[b] | LCST[c] (intact) | LCST[c] (degraded) | Tg (° C.) (intact) | Tg (° C.) (degraded) |
|---|---|---|---|---|---|---|
| pNNAD-4 (80:4:12:4) | 76.0:3.4:14.7:3.9 | 26563 | 21.25 | 0 | 94.28 | 98.62 |
| pNNAD-8 (80:4:8:8) | 74.8:4.1:12.9:8.2 | 28494 | 16.98 | 0 | 90.78 | 97.81 |
| pNNAD-12 (80:4:4:12) | 75.2:3.8:8.6:12.4 | 30776 | 13.11 | 0 | 87.63 | 100.94 |

[a]Copolymer composition in mol % determined by $^1$H NMR,
[b]$M_n$ obtained from Gel permeation chromatography (GPC),
[c]LCST obtained from DSC.

Copolymer Molecular Weight

To determine copolymer molecular weight, organic phase GPC was initially selected as temperature-induced phase transition properties of the pNNAD copolymers in aqueous conditions prevented the use of aqueous phase GPC. However, organic phase GPC with both THF and DMF solvents yielded highly irregular and inconsistent molecular weight measurements with values exceeding one million Da. Therefore, the copolymers were subjected to accelerated hydrolysis to remove phase transition properties, thereby allowing MW assessment via aqueous phase GPC. Copolymer molecular weights are presented in Table 1. MW measurements were obtained using hydrolyzed pNNAD copolymers, therefore the resulting MW will be slightly lower than fully intact copolymers. However, the initial copolymer MW can easily be quantified by calculating the MW of the degraded copolymer side groups that were hydrolyzed.

Figure 2:
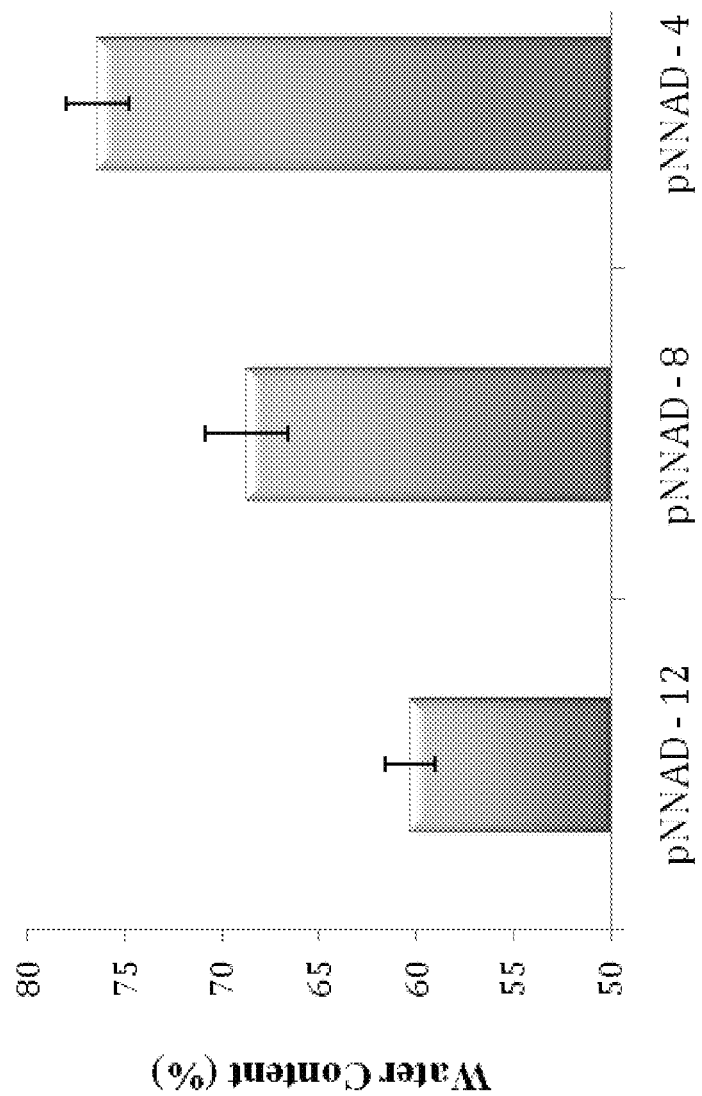
FIG. 2 graphically illustrates that water content of various pNNAD copolymers measured gravimetrically was found to be highly dependent on DBA content.

Water Content:

The water content of the pNNAD copolymers was assessed gravimetrically and was found to be strongly dependent on DBA content, as shown in FIG. 2, consistent with thermal transition properties. As the copolymer DBA content increased, the hydrophobic nature of the copolymer increased, thereby decreasing the water content and lowering the LCST.

Glass transition temperatures (Table 1) of intact and degraded pNNAD copolymers were examined by DSC and were found to be dependent on AA and DBA content. Intact copolymers with a higher AA/DBA ratio were found to have higher Tg due to increased hydrophilicity and increased water content. However, after degradation, all copolymers were reduced to similar NIPAAm and AA content as DBA and NAS groups were hydrolyzed to form AA. As a result, copolymer Tg for all copolymers following degradation was approximately the same.

Physiological and Accelerated pNNAD Degradation Mechanisms

The proposed copolymer degradation mechanisms of pNNAD in both physiological and harsh basic conditions are illustrated in FIG. 1. It is proposed that under physiologic conditions, hydrolytic ring opening of the DBA co-monomer significantly alters the phase transition properties of the copolymer as the DBA side chain transitions from a hydrophobic lactone ring to a hydrophilic carboxylic acid group. The resulting increase in copolymer LCST initiates a reverse phase transition process, inducing the solid cell or drug scaffold to re-hydrate, allowing the copolymer to be cleared from the eye through the anterior ocular elimination route. From here, the copolymer enters the systemic circulation and is ultimately cleared from the body via the kidneys.

FT-IR was used to confirm the final structure of the various pNNAD copolymers as well as to examine the changes in copolymer structure as a function of accelerated degradation. The pNNAD-4 spectrum shows characteristic NIPAAm peaks of C=O and N—H stretching of the amide groups I and II around 1658 and 1540 $cm^{-1}$ respectively. Additionally, stretching vibration of the N—H amine group appears near 3309 $cm^{-1}$, and the isopropyl group is present near 1460, 1380, and 1360 $cm^{-1}$. Characteristic succinimide peaks from the NAS copolymer were observed near 1812, 1781 and 1735 $cm^{-1}$. The carbonyl group from AA was observed near 1710 $cm^{-1}$. The two DBA characteristic peaks, specifically the carbonyl peak in the ring structure and the carbonyl peak connected to the polymer backbone, overlap with the succinimide peak around 1781 and 1735 $cm^{-1}$ respectively. Upon partial hydrolytic degradation of pNNAD-4 achieved through accelerated degradation in harsh basic conditions, DBA ring opening led to a decrease in the carbonyl peak in the DBA ring and an increase in the carboxylic acid C=O peak around 1652 $cm^{-1}$. Complete pNNAD degradation led to the disappearance of the DBA carbonyl peak and the production of a broad carboxylic acid C=O peak around 1652 $cm^{-1}$. During the accelerated degradation process, the pH was adjusted to 10.5 daily with 1M or 0.1M NaOH. Decreases in the pH of roughly 1 unit were observed in the first few days of the process, followed by smaller decreases over the next couple of weeks and finally equilibrium was achieved after 21 days, indicating complete copolymer degradation had been achieved.

Figure 3:
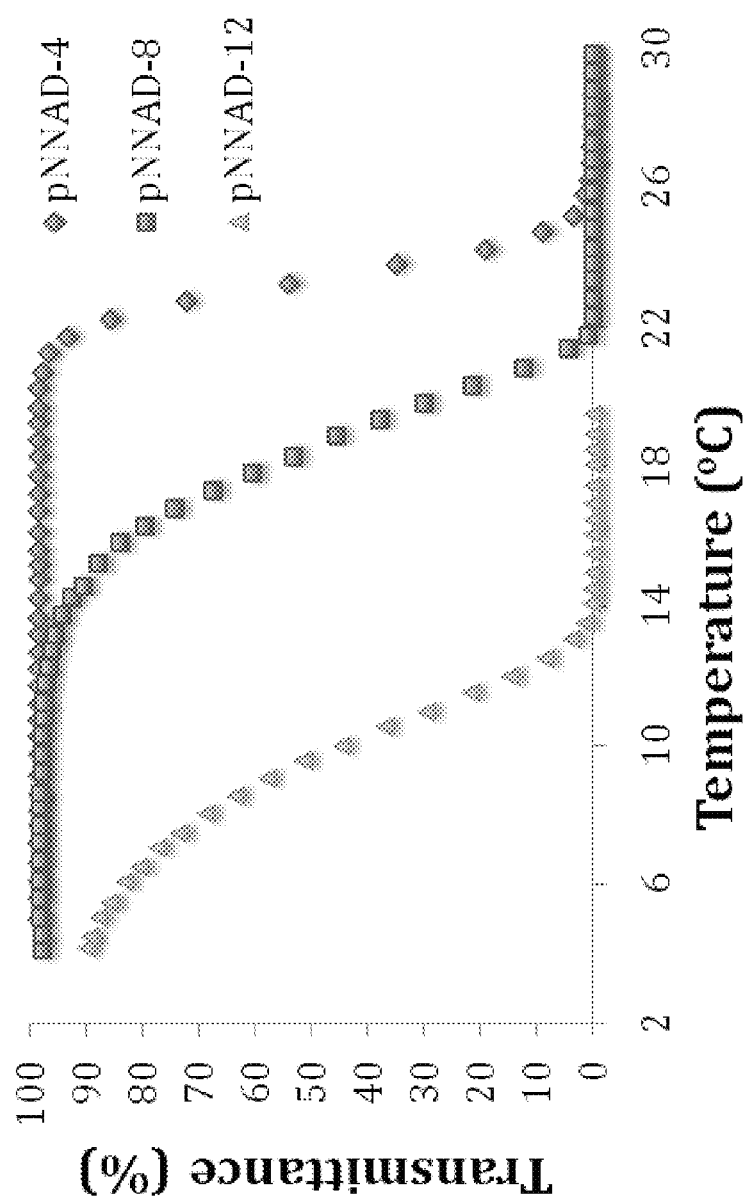
FIG. 3 graphically illustrates transmittance measurements of the various pNNAD copolymers as a function of increasing temperature.

The sequential degradation mechanism of pNNAD copolymers in harsh basic conditions was also characterized by $^1$H NMR. In the pNNAD-4 spectra, two characteristic peaks from hydrogen (CH and $CH_2$) within the DBA ring can be seen between 5.2-5.7 ppm and 3.8-4.1 ppm respectively. Upon hydrolytic ring opening as a result of accelerated copolymer degradation, these characteristic DBA ring peaks decrease in magnitude and the CH peak shifts to 4.3-4.7 ppm. Furthermore, the new $CH_2$ peak from the former DBA ring appears at 3.0-3.5 confirming successful ring opening while the ester linkage remains intact with the polymer backbone. Complete degradation was confirmed with the disappearance of these two DBA ring proton peaks (CH and $CH_2$), with a resulting spectra of poly(NIPAAm-co-AA). Both pNNAD-8 and pNNAD-12 show similar degradation trends (data not shown).

pNNAD Copolymer Phase Transition Properties:

The copolymer phase transition properties were characterized by both DSC and UV spectrophotometry. LCST values obtained via DSC are reported in Table 1 and the transmittance curves as a function of increasing temperature are shown in FIG. 3. DBA content had a strong influence on pNNAD LCST; increasing DBA content increased the hydrophobic content of the copolymer, which decreased the LCST. All copolymers were found to have sub-physiological phase transition temperatures, which is a requirement for in situ forming hydrogel scaffolds that utilize body temperature as the stimuli to induce phase transition. The sudden decrease in transmittance as the copolymers are heated above their LCST provides evidence that the copolymers undergo a rapid phase transition from liquid to gel. This finding was supported during our in vivo injections in which robust polymer gels were formed almost instantly following injection into SKH1-E mice.

Rapid gelling kinetics are useful for in situ forming hydrogels in order to entrap the maximum amount of delivered pharmaceutical. Unlike pre-formed drug releasing scaffolds, which are loaded with a drug ex vivo, the pNNAD copolymers are simply infused with a drug solution and gel following injection to form a solid drug depot in situ while preventing the mass efflux of free drug into the surrounding environment. In the present studies, gelation was observed upon injection of 20% pNNAD copolymers into pre-heated aqueous solutions without syringe clogging using needles of gauge 18-27.

Figure 4:
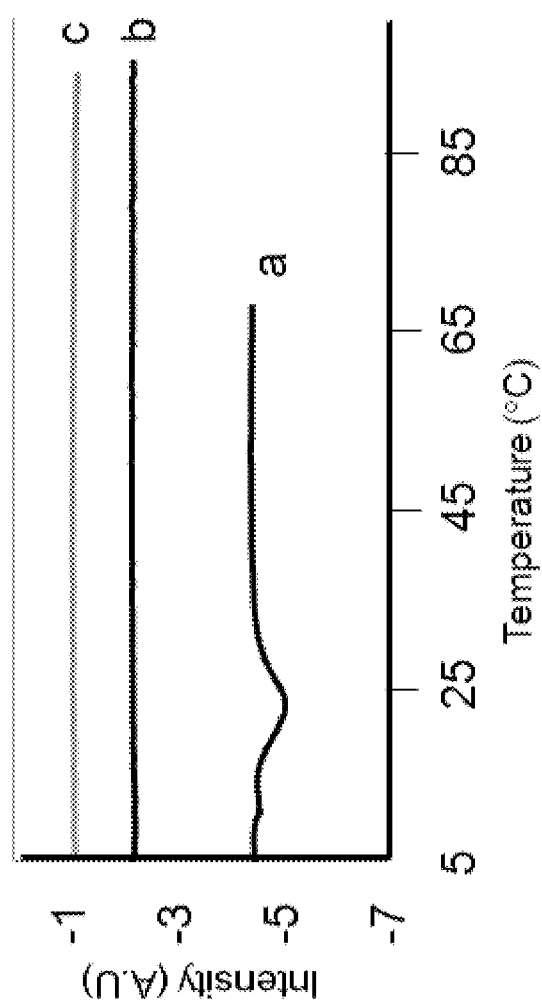
FIG. 4 illustrates the results of a DSC analysis revealing an LCST commencing around 21° C. for intact pNNAD-4 (a) and the complete removal of phase transition properties following partial degradation (b) and complete hydrolysis (c)

Following partial and complete degradation via accelerated hydrolysis, there was no observable LCST between 0-100° C. as assessed by DSC (FIGS. 4b and c respectively). This finding is significant as it demonstrates that the first stages of pNNAD degradation, which were revealed by $^1$H NMR to occur through hydrolytic ring opening of the DBA side chain, are sufficient to eliminate the thermoresponsive nature of the copolymer between 0-100° C. Therefore, as the DBA ring opens, the gelled copolymer will revert back into a liquid state allowing its clearance from the eye, uptake into systemic circulation and ultimate removal from the body via the kidneys, without producing low molecular weight byproducts.

Copolymer Degradation Studies

Copolymer degradation kinetics were studied by dissolving the pNNAD copolymers in 20% w/v of PBS (pH 7.4). The samples were maintained in a 37° C. incubator for 5, 20, 40, 65 and 130 days. At the specified time-points, the PBS supernatant was aspirated to remove PBS as well as any pNNAD copolymer that had undergone hydrolytic DBA ring opening and transitioned back into a soluble state. The samples were then carefully rinsed with a pre-heated de-ionized water solution to remove residual PBS and hydrolyzed pNNAD. The copolymers were dried to constant dry weight and the mass remaining was calculated according to equation 2 (FIG. 5).

Figure 5:
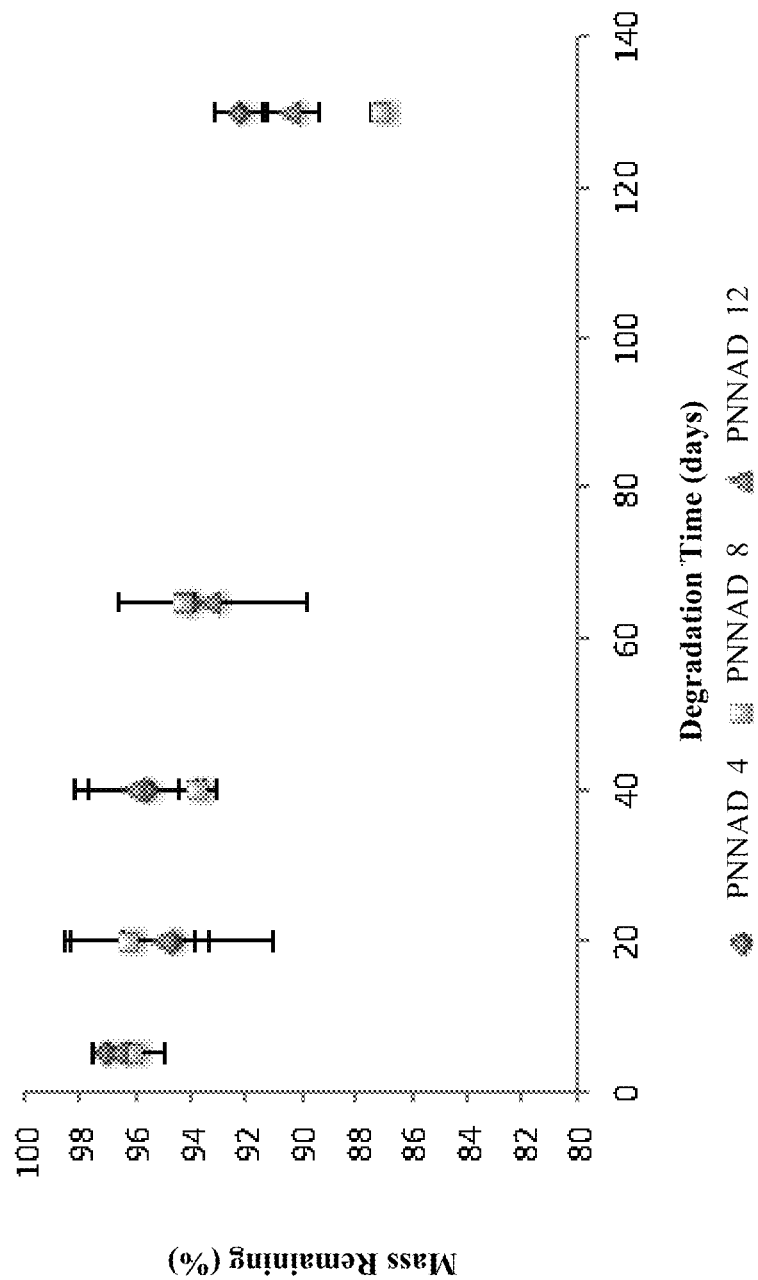
FIG. 5 illustrates pNNAD copolymer degradation kinetics determined by assessing mass loss as a function of time in 37° C. PBS.
Figure 6:
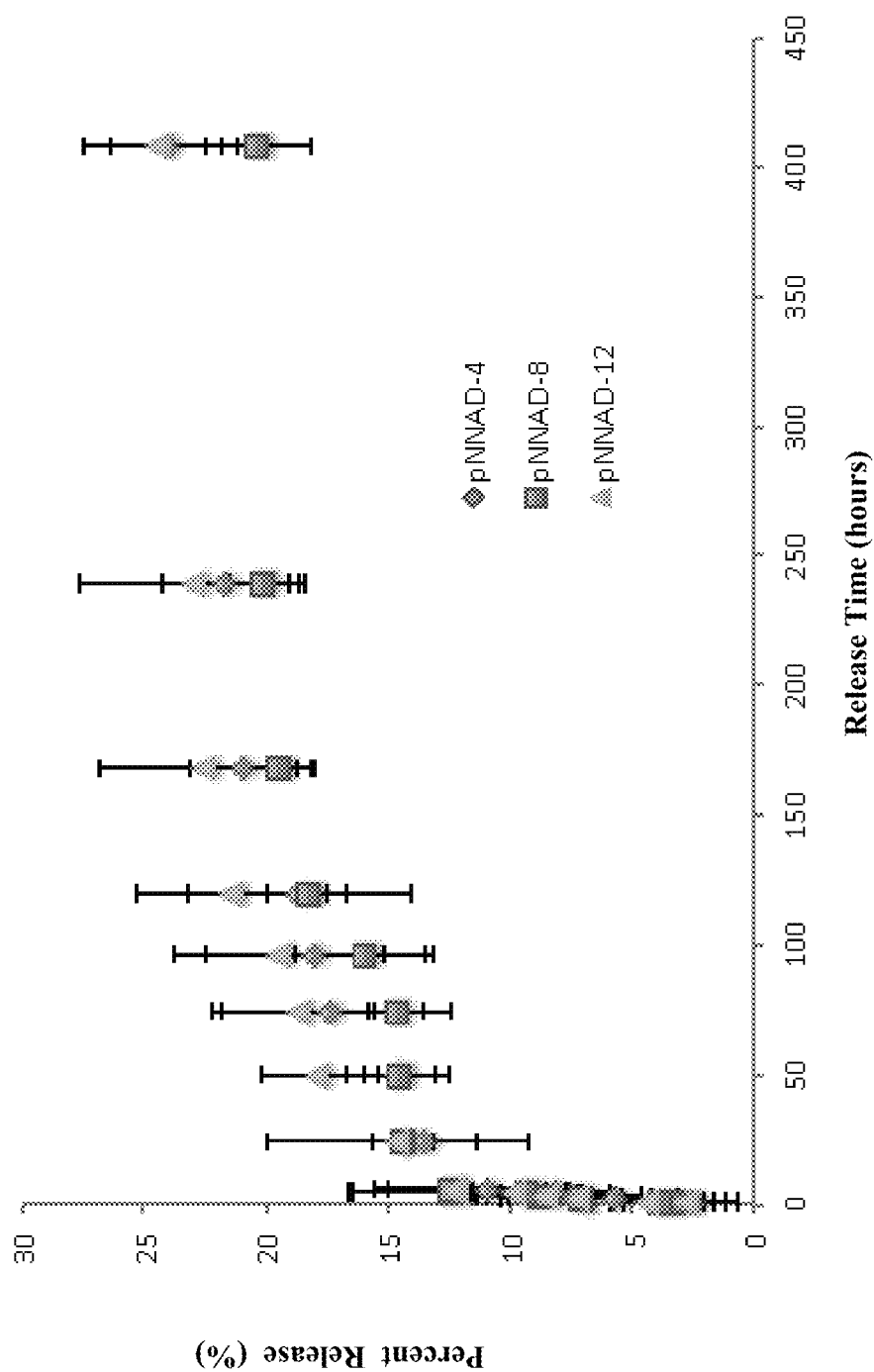
FIG. 6 illustrates dexamethasone release from the various pNNAD systems.

It is apparent from FIG. 5 that in a heated PBS environment, hydrolytic ring opening of the DBA side chain occurs slowly. All scaffolds maintained over 85% of their initial mass after 130 days in heated PBS. As discussed, this slow degradation is highly favorable for ocular drug delivery as it may be conducive to providing long-term sustained release of low-levels of drug, minimizing the frequency of intravitreal injections.

SEM images of the dried pNNAD copolymers were collected at each time point in the degradation study to assess changes in morphology as a function of degradation. The SEM micrographs reveal subtle changes in copolymer morphology as a function of time, limited changes in a 130 day period. These small changes are most apparent in the pNNAD-4 copolymer, which had the lowest DBA content. There is evidence of increased pitting and surface erosion in pNNAD-4, and to some extent pNNAD-8, at day 130. As expected, surface degradation in the pNNAD-12 copolymer, which has the highest DBA content and lowest water content, appears to be less evident than the other two materials. The pNNAD-8 and pNNAD-12 day 40 images were taken of fractures that occurred as a result of sample handling that exposed internal copolymer morphology. The internal copolymer structure does not reveal the same pitting morphology observed on the surface, possibly indicating that erosion occurs primarily on the surface as expected, where there is the greatest amount of water to hydrolyze the DBA lactone ring. However, in the pNNAD-12 copolymer there was little evidence of morphological change.

None of the copolymers undergo dramatic morphological changes over the course of 130 days in heated PBS, consistent with the relatively minor extent of mass loss observed throughout the experiment. As the copolymers continue to hydrolyze, their surfaces will erode and become more porous, increasing the surface area through which drugs can diffuse and increasing the release rate. For long-term, sustained release, slow degrading materials that do not undergo rapid changes in morphology are desirable to maintain relatively controlled release rates for extended periods of time.

Drug and Protein Delivery

Corticosteroids are thought to combat macular edema through suppression of vascular endothelial growth factor (VEGF) expression, which has been shown to play a key role in ocular neovascularization, and through stabilization of the BRB. Therefore, dexamethasone, which is a small (392.5 Da) hydrophobic corticosteroid being examined for its potential to treat diabetic macular edema (DME), was selected as a model drug to examine the release profile of pNNAD copolymers. As mentioned, free drug suspensions within the eye can cause a number of complications; however, entrapment within a hydrogel scaffold that slowly releases low levels of drug for sustained periods of time can significantly decrease the amount of free drug present within the vitreous and decrease the associated risk. As, expected, the pNNAD release curve (see FIG. 7) reveals a small initial burst, which may be helpful in treating the initial hostile environment within the compromised eye by decreasing the elevated VEGF expression and stabilization of the BRB. The subsequent stabilization in the release curve ideally produces a slow-releasing scaffold capable of maintaining low levels of drug that are sufficient to sustain a therapeutic concentration within the vitreous for extended periods of time.

Figure 7:
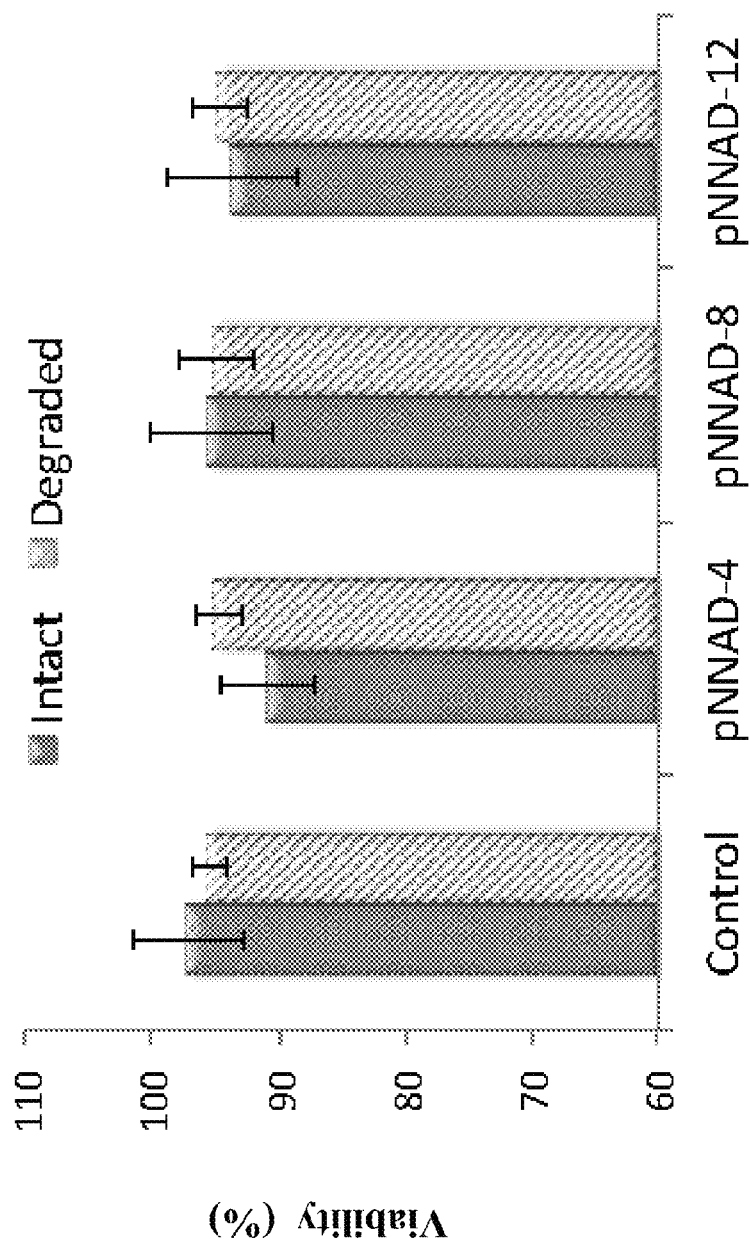
FIG. 7 graphically illustrates the compatibility of intact and fully degraded pNNAD copolymers with RPE cells in culture.

In Vitro Cell Viability:

In vitro testing of the pNNAD copolymers revealed excellent compatibility with RPE cells (see FIG. 7). Copolymer scaffolds were dissolved in the supernatant of pre-adhered cells and incubated for 96 hours. Viability remained above 90% for all samples tested. Additionally, RPE cells were found to be compatible in culture with the copolymers as they transition through the different stages of hydrolytic degradation from partial to complete hydrolysis (partially degraded pNNAD data not shown).

Conjugation of pNNAD copolymers with RGDS Cell Adhesion Peptides

Figure 8:
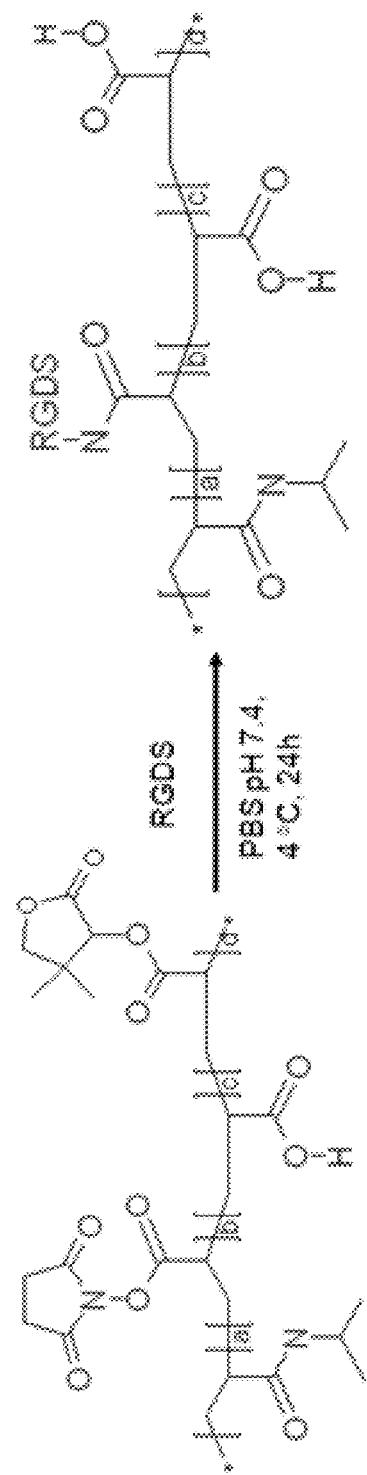
FIG. 8 illustrates a reaction scheme for the conjugation of RGDS cell adhesive peptides along the pNNAD copolymer backbone.

The conjugation reaction of RGDS peptides to the pNNAD copolymer is illustrated in the schematic set out in FIG. 8. The RGDS grafting density on the pNNAD-4 and pNNAD-12 copolymers was determined to be 2 and 1.7 mol % of the total monomer content respectively. Although water content and phase transition properties for RGDS-conjugated pNNAD copolymers was not analyzed, based on previous studies, incorporation of the cell adhesion peptide is expected to slightly increase copolymer water content and LCST. However, the small increase in LCST did not raise the critical gelling temperature above body temperature, suggesting that the RGDS-conjugated pNNAD copolymers were useful for application as injectable, in situ gelling scaffolds. This was confirmed with in vivo experiments in which RGDS-conjugated pNNAD-4 and -12 copolymers gelled almost immediately upon injection into SKH1-E mice.

Subcutaneous Implantation into Mice

In vivo testing of pNNAD-4 and pNNAD-12 copolymers, both RGDS-conjugated and unmodified, was performed via subcutaneous injection between the shoulder blades of SKH1-E mice. All samples were successfully injected using a 25 gauge needle and formed a mechanically robust gel beneath the skin. The gel appeared to spread out into a thin film underneath the skin over the course of the study, presumably as a result of being compressed between the dermal layers. For subretinal cell therapeutics, this scaffold spreading is favourable as it allows single injections to treat a relatively large area. However, polymer spreading would not be suitable for drug delivery purposes, as a thin film with a large surface area would quickly release the infused drug. In the absence of compressive forces, polymer thinning was not observed; in the drug release and degradation assays in vitro, copolymers maintained their initial shape throughout the experiment. The absence of compressive forces within the intravitreal environment is expected to allow injected copolymers to maintain their gelled morphology, although this will be examined in future studies.

While material spreading is desirable for subretinal cell therapy, it made it identification of the injected copolymer and subsequent histological analysis of the surrounding tissues difficult. Therefore, histological sections were obtained from the best estimate of the polymer location within the tissues. The tissue from the injection site where the polymer scaffold was expected to reside was excised and analyzed. Although discrete polymer gels were not apparent, histological analysis of the tissue at the injection site did not reveal any observable adverse response to subcutaneous copolymer injections.

CONCLUSION

Several thermo-responsive copolymers based on NIPAAm, NAS and varying compositions of AA and DBA were synthesized for application in posterior segment ophthalmic cell and drug delivery therapeutics. These copolymers were designed to address the serious need for improved delivery modalities to provide sustained therapeutic concentrations of drug within the eye and reduce the frequency of intravitreal injections. All pNNAD copolymers possess subphysiological phase transition temperatures, allowing minimally invasive delivery of cell or drug suspensions into the back of the eye, followed by temperature-induced scaffold formation and entrapment of the infused therapeutic. RGDS-conjugated pNNAD copolymers provide a cell-adhesive thermoresponsive material designed to allow transplantation and support of anchorage-dependant RPE cells into the delicate subretinal space. Non-conjugated pNNAD copolymers were designed to act as a solid drug-depot that could be injected into the eye to provide long-term, localized release of low levels of pharmaceuticals to decrease the frequency of intravitreal injections required to maintain therapeutic concentrations of drug within the posterior segment of the eye. All copolymers were designed to undergo a process of hydrolytic ring opening through the DBA co-monomer, resulting in a hydrolysis dependant LCST increase that initiates scaffold re-hydration and clearance from the body without the release of low molecular weight degradation products. The copolymers did not appear to elicit any observable adverse response following subcutaneous injection into SKH1-E mice as examined via histological analysis using H&E staining. These results indicate the utility of these copolymers as delivery vehicles to transport cell and drug suspensions into the back of the eye.

References referred to herein are incorporated by reference.

We claim:

1. A polymer system useful for in vivo delivery of a therapeutic agent, wherein the polymer system comprises at least one transition co-monomer in an amount of about 50-99.5% by weight that renders the polymer system capable of reversible stimuli induced transition from a liquid to a gel, and an acrylated lactone-containing co-monomer in an amount of about 0.5-15% by weight, an amine-reactive co-monomer in an amount of up to about 15% by weight and a hydrophilic co-monomer in an amount up to about 15% by weight, wherein the transition co-monomer, amine-reactive co-monomer, hydrophilic co-monomer and the acrylated lactone-containing co-monomer are polymerized within the polymer system and wherein the lactone ring of the acrylated lactone-containing co-monomer exists as a side chain within the polymer system which is subject to hydrolytic ring opening but remains attached to the polymer system to transition the polymer system from a gel to a liquid under physiological conditions.

2. The polymer system of claim 1, wherein the transition co-monomer is a co-monomer of a polymer selected from the group consisting of an acrylic-based polymer, a polyurethane, a polyurethane urea, a silicone polymer, a polyvinyl alcohol and protein-based polymer.

3. The polymer system of claim 2, wherein the acrylic-based polymer is selected from the group consisting of polymethylmethacrylate, poly(hydroxyethyl methacrylate) (pHEMA), poly N-isopropyl acrylamide (NIPAAm) and polyacrylic acid.

4. The polymer system of claim 1, wherein the acrylated lactone-containing co-monomer is acryloyloxy dimethyl-γ-butyrolactone (DBA).

5. The polymer of claim 1, wherein the amine-reactive co-monomer is a succinide-containing monomer.

6. The polymer of claim 1, wherein a therapeutic agent is bound to the polymer.

7. The polymer of claim 1, additionally comprising an amine-terminated cell-adhesion agent.

8. The polymer of claim 7, wherein the cell-adhesion agent is selected from the group consisting of RODS, REDV, YIGSR, IKVAV and GFOGER.

9. The polymer of claim 1, which transitions from a liquid to a gel at a temperature that is greater than room temperature.

10. A method of delivering a therapeutic agent to a target site in vivo comprising administering a polymer system as a solution to the target site,
wherein the polymer system comprises at least one transition co-monomer in an amount of about 50-99.5% by weight that renders the polymer system capable of reversible stimuli induced transition from a liquid to a gel, and an acrylated lactone-containing co-monomer in an amount of about 0.5-15% by weight, an amine-reactive co-monomer in an amount of up to about 15% by weight and a hydrophilic co-monomer in an amount up to about 15% by weight, wherein the transition co-monomer, amine-reactive co-monomer, hydrophilic co-monomer and the acrylated lactone-containing co-monomer are polymerized within the polymer system and wherein the lactone ring of the acrylated lactone-containing co-monomer exists as a side chain within the polymer system which is subject to hydrolytic ring opening but remains attached to the polymer system to transition the polymer system from a gel to a liquid under physiological conditions; and
wherein the polymer system comprises a therapeutic agent.

11. The method of claim 9, wherein the transition co-monomer forms an acrylic-based polymer selected from the group consisting of polymethylmethacrylate, poly(hydroxyethyl methacrylate) (pHEMA), poly N-isopropyl acrylamide (NIPAAm) and polyacrylic acid, and the degradable co-monomer is selected from the group consisting of lactone-containing co-monomer, poly(lactic acid), poly(glycolic acid), poly(glycolic-co-lactic acid), poly(caprolactone), [poly(dioxanone), poly(3-hydroxybutyrate), poly(3-hydroxyvalcrate), poly(valcrolactone), poly(tartonic acid), poly (malonic acid)], poly(anhydrides), poly(orthoesters) and polyphosphazenes.

12. The method of claim 9, wherein the polymer comprises amine-reactive co-monomer to which the therapeutic agent is bound.

13. The method of claim 9, wherein the polymer transitions from a liquid to a gel on administration to the target site.

* * * * *